US010835685B2

(12) United States Patent
Ring

(10) Patent No.: US 10,835,685 B2
(45) Date of Patent: Nov. 17, 2020

(54) THERMAL SPRING RELEASE MECHANISM FOR A DRUG DELIVERY DEVICE

(71) Applicant: AMGEN INC., Thousand Oaks, CA (US)

(72) Inventor: Lawrence Scott Ring, Laguna Beach, CA (US)

(73) Assignee: AMGEN INC., Thousand Oaks, CA (US)

( * ) Notice: Subject to any disclaimer, the term of this patent is extended or adjusted under 35 U.S.C. 154(b) by 114 days.

(21) Appl. No.: 15/993,258

(22) Filed: May 30, 2018

(65) Prior Publication Data

US 2019/0366011 A1 Dec. 5, 2019

(51) Int. Cl.
*A61M 5/315* (2006.01)
*A61M 5/20* (2006.01)
*A61M 5/24* (2006.01)
*A61M 5/142* (2006.01)

(52) U.S. Cl.
CPC .......... *A61M 5/31578* (2013.01); *A61M 5/20* (2013.01); *A61M 5/31566* (2013.01); *A61M 5/14248* (2013.01); *A61M 5/24* (2013.01); *A61M 2005/206* (2013.01); *A61M 2005/2026* (2013.01); *A61M 2205/3653* (2013.01)

(58) Field of Classification Search
CPC .......... A61M 5/31578; A61M 5/31566; A61M 5/24; A61M 2005/2026; A61M 2005/2073; A61M 5/315; A61M 2005/1584; A61M 5/155; A61M 5/31501; A61M 5/20; A61M 2005/206
See application file for complete search history.

(56) References Cited

U.S. PATENT DOCUMENTS

| | | | |
|---|---|---|---|
| 3,742,948 A * | 7/1973 | Post | A61M 5/2033 604/139 |
| 4,747,838 A | 5/1988 | Wolff et al. | |
| 4,772,263 A | 9/1988 | Dorman et al. | |
| 2008/0058719 A1* | 3/2008 | Edwards | A61M 5/19 604/140 |
| 2008/0097312 A1* | 4/2008 | Wilmot | A61M 5/2033 604/117 |
| 2010/0049125 A1* | 2/2010 | James | A61M 5/2033 604/110 |
| 2011/0054414 A1* | 3/2011 | Shang | A61M 5/315 604/218 |

(Continued)

FOREIGN PATENT DOCUMENTS

| | | | | |
|---|---|---|---|---|
| GB | 2463034 A * | 3/2010 | ........ | A61M 5/31511 |
| WO | WO-2012030277 A1 * | 3/2012 | .......... | A61M 5/3146 |

OTHER PUBLICATIONS

International Application No. PCT/US19/28603, International Search Report and Written Opinion, dated Aug. 2, 2019.

*Primary Examiner* — Nathan R Price
*Assistant Examiner* — Jacob Michael Lindsay
(74) *Attorney, Agent, or Firm* — Marshall, Gerstein & Borun LLP

(57) ABSTRACT

A spring release mechanism for a drug delivery includes a fusible member to restrain a spring in a charged state. A heating element is utilized to selectively heat and sever the fusible member. When the fusible member is severed, the spring is allowed to discharge and drive the drug delivery device components operably coupled thereto.

10 Claims, 7 Drawing Sheets

(56) References Cited

U.S. PATENT DOCUMENTS

| | | | | |
|---|---|---|---|---|
| 2011/0313364 A1* | 12/2011 | Rolfe | ............. | A61M 5/2033 |
| | | | | 604/198 |
| 2012/0016296 A1* | 1/2012 | Charles | ............. | A61M 5/2066 |
| | | | | 604/87 |
| 2013/0018313 A1* | 1/2013 | Kramer | ............. | A61M 5/2033 |
| | | | | 604/131 |
| 2013/0060231 A1* | 3/2013 | Adlon | ............. | A61M 5/3234 |
| | | | | 604/506 |
| 2013/0317480 A1* | 11/2013 | Reber | ............. | A61M 5/2033 |
| | | | | 604/506 |
| 2014/0046259 A1* | 2/2014 | Reber | ............. | A61M 5/2033 |
| | | | | 604/136 |
| 2014/0207104 A1* | 7/2014 | Vouillamoz | ............. | A61M 5/3286 |
| | | | | 604/506 |
| 2014/0323978 A1* | 10/2014 | Henley | ............. | A61M 5/2033 |
| | | | | 604/198 |
| 2014/0330216 A1* | 11/2014 | Weaver | ............. | A61M 5/31513 |
| | | | | 604/198 |
| 2015/0272830 A1* | 10/2015 | Iordanov | ............. | G06F 19/3462 |
| | | | | 221/1 |
| 2015/0283323 A1* | 10/2015 | Young | ............. | A61M 5/2033 |
| | | | | 604/182 |
| 2016/0235916 A1* | 8/2016 | Edwards | ............. | A61M 5/19 |
| 2016/0361496 A1* | 12/2016 | Guillermo | ............. | A61M 5/2046 |
| 2017/0014575 A1* | 1/2017 | Hansen | ............. | A61M 5/20 |
| 2017/0143900 A1* | 5/2017 | Rioux | ............. | A61M 5/1723 |
| 2017/0361029 A1* | 12/2017 | Benito | ............. | A61M 5/3286 |
| 2018/0133395 A1 | 5/2018 | Margairaz et al. | | |

* cited by examiner

THERMAL SPRING RELEASE MECHANISM FOR A DRUG DELIVERY DEVICE

FIELD OF THE DISCLOSURE

The present disclosure generally relates to drive mechanisms for drug delivery devices and, more particularly, to spring driven drive mechanisms for drug delivery devices.

BACKGROUND

Drug delivery devices, such as on-body injectors and autoinjectors, can utilize an electromechanically controlled delivery system to drive a plunger rod and a stopper through a reservoir to dispense a predetermined amount of drug and to insert/retract a needle or cannula. These electromechanically controlled delivery systems can be complicated with a variety of mechanical components, such as motors, gears, cables, capstans, telescoping drives, lead screws, drive nuts, shape memory alloy wires, and so forth. The delivery system can further include associated electronics and the power needed to operate the electronics. Accordingly, there is a need for a high-reliability, small size, and low cost delivery device.

SUMMARY

In accordance with a first aspect, a drive apparatus for a drug delivery device is disclosed that includes a spring, a body coupled to the spring, a retaining member configured to engage the body to hold the spring in a charged state, and a fusible member operably coupled to the body to restrict movement of the retaining member, the fusible member configured to be selectively heated and severed to release the retaining member and allow the spring to release from the charged state.

In accordance with a second aspect, a method for releasing a drive spring for a drug delivery device is disclosed that includes coupling a body to a spring and engaging the body with a retaining member to hold the spring in a charged state. The method further includes heating and severing a fusible member that is operably coupled to a body to restrict movement of the retaining member and releasing the retaining member to release the spring from the charged state.

The above first and second aspects can further include one or more of the following. According to some forms, the spring can be a torsion spring or a compression spring. According to further forms, the drive apparatus can include a needle insertion mechanism where the release of the spring from the charged state drives operation of the needle insertion mechanism and/or a fluid pathway assembly including a container and needle where the release of the spring from the charged state causes the needle to be inserted into the container to establish a fluid pathway. According to another form, the body can be a plunger rod and the release of the spring from the charged state can drive the plunger rod. The spring can directly drive operation of a mechanism/assembly as described herein and/or can cause a gas cylinder to be punctured to thereby establish a gas pathway for a gas-driven, pneumatic system.

In accordance with a third aspect, a plunger rod drive apparatus for a drug delivery device is disclosed that includes a plunger rod having an elongate body with an outwardly extending plunger face at a distal end and forked configuration at a proximal end. The apparatus further includes a fusible member that extends across the forked configuration at the proximal end of the plunger rod, a spring mounted around the elongate body of the plunger rod abutting the plunger face, and a retaining member that extends through the forked configuration of the plunger rod between the spring and the fusible member. The retaining member holds the spring in a compressed configuration. The apparatus further includes a heating element that is configured to heat the fusible member and cause the fusible member to sever allowing the retaining member to pass through the proximal end of the plunger rod and release the spring to drive the plunger rod.

According to some forms, the fusible member can be integral with the plunger rod or can be mounted to the proximal end of the plunger rod.

According to further forms, the forked configuration can include opposing prongs having inwardly projecting feet that are configured to engage the retaining member and the retaining member can be a box-shaped member having chamfered edges configured to engage the inwardly projecting feet of the prongs. According to a further form, the retaining member can include engagement portions that extend along exterior side surfaces thereof. The inwardly projecting feet of the prongs are configured to sequentially engage the engagement portions to restrict movement of the retaining member through the proximal end of the plunger rod.

According to another form, the heating element can be a heating wire extending along a top surface of the retaining member and between the retaining member and the fusible member or contact electrodes exposed on an upper surface of the retaining member.

According to another form, any apparatus above can be provided in combination with a plunger assembly, where the plunger assembly includes a reservoir and a stopper that is received within the reservoir, such that the plunger face of the plunger rod is configured to engage the stopper.

In accordance with a fourth aspect, a method of assembling a plunger rod drive apparatus for a drug delivery device is disclosed that includes providing a plunger rod having an elongate body with an outwardly extending plunger face at a distal end and forked configuration at a proximal end, and a fusible member extending across the forked configuration at the proximal end of the plunger rod. The method further includes mounting a spring coaxially around the elongate body of the plunger rod abutting the plunger face, compressing the spring to a compressed configuration, and inserting a retaining member through the forked configuration of the plunger rod between the spring and the fusible member, where the retaining member holding the spring in a compressed configuration. The method further includes disposing a heating element adjacent to the fusible member, where the heating element is selectively operable to cause the fusible member to sever to thereby allow the retaining member to pass through the proximal end of the plunger rod and releasing the spring to drive the plunger rod.

According to some forms, providing the plunger rod can include providing a plunger rod with the fusible member being integral with the proximal end or mounting the fusible member to the proximal end of the plunger rod.

According to another form, the method can further include engaging the retaining member with inwardly projecting feet of opposing prongs of the forked configuration.

According to further forms, disposing the heating element adjacent to the fusible member can include disposing a wire along a top surface of the retaining member and between the retaining member and the fusible member or disposing a plurality of contact electrodes on an upper surface of the retaining member to electrically engage the fusible member.

In accordance with a fifth aspect, a method for dispensing a medicament is disclosed that includes causing a heating element to heat and severing a fusible member to release a retaining member from a stored position holding a spring in a compressed state. The method further includes driving a plunger rod with the spring, engaging a stopper with the plunger rod, and driving the stopper through a reservoir containing the medicament.

According to one form, causing the heating element to heat comprises receiving an actuation signal at a controller from a user input of a drug delivery device and supplying electrical energy to a heating element adjacent the fusible member with the controller.

BRIEF DESCRIPTION OF THE DRAWINGS

The above needs are at least partially met through provision of the embodiments described in the following detailed description, particularly when studied in conjunction with the drawings, wherein.

Figure 1:
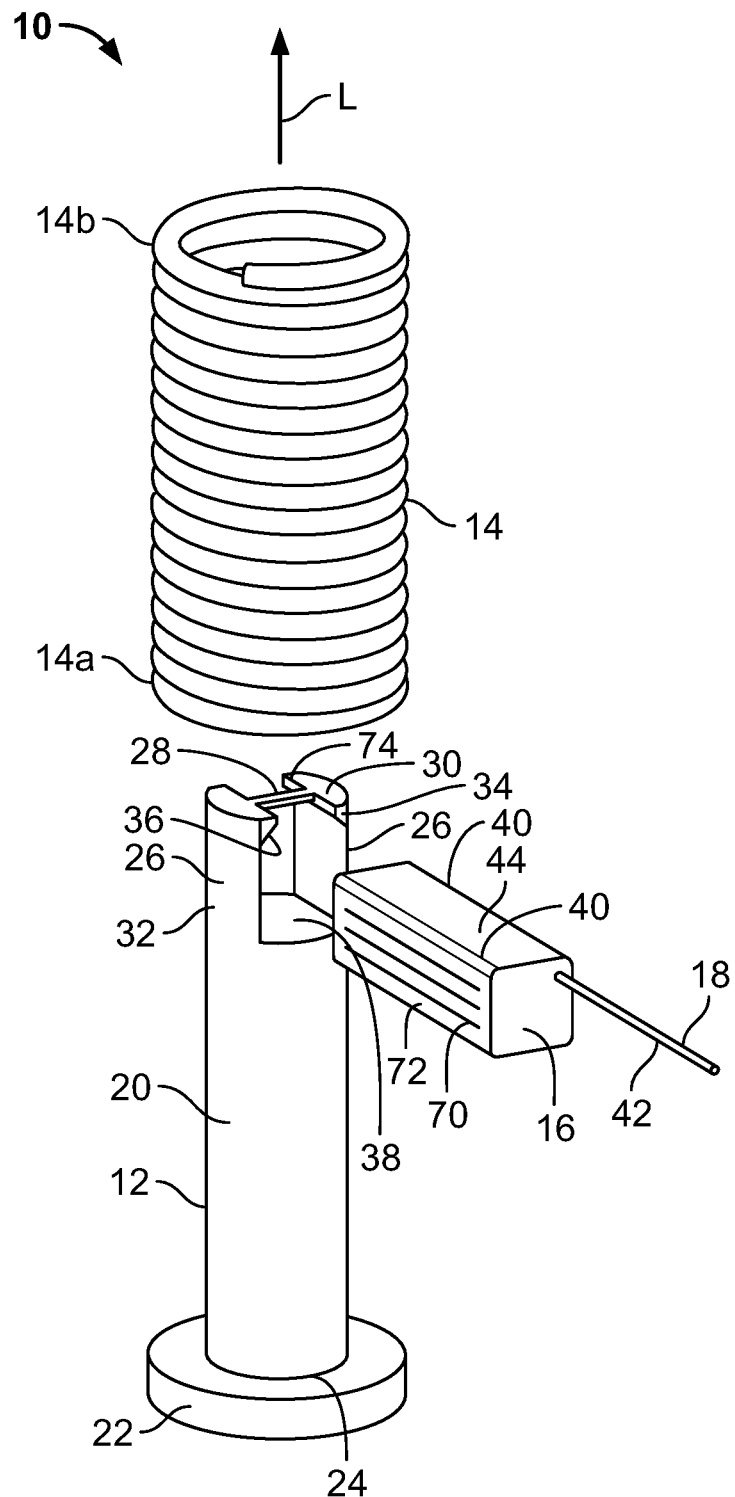
FIG. 1 is an exploded perspective view of one embodiment of a compression spring drive assembly in accordance with various embodiments.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

A spring release mechanism for a drug delivery device is provided that is smaller, more reliable, and uses less energy than conventional drives. The release mechanism uses a fusible member to restrain a spring in a charged configuration. A heating element is utilized to selectively heat and sever the fusible member in response to a user actuation and/or at a programmed time. When the fusible member is severed, the spring is allowed to discharge and drive drug delivery device components operably coupled thereto. This configuration eliminates many of the components needed for conventional drives and lowers power consumption. More specifically, a small amount, such as a single pulse, of power through the heating element severs the fusible member. This configuration allows for a smaller battery as compared to conventional drives, fits in a much smaller physical volume, has higher reliability due to the reduce complexity and limited number of parts, and is much lower in cost.

The single use spring release mechanism can be adapted for different spring types. Compression and torsion springs can be adapted to drive operation of any suitable drug delivery device, several embodiments of which are discussed in detail below. In one example, the spring can be a compression spring and the release mechanism can be utilized to provide a delayed drive of a plunger rod for the drug delivery device for a bolus drug delivery at a programmed time. In this form, the spring can be held in a compressed state coaxially extending around a plunger rod at least in part by the fusible member. In another example, the spring can be a torsion spring and the release mechanism can be utilized to drive a needle and/or cannula insertion assembly. In this form, the spring can have one end held in a fixed position and the fusible member can hold the other end of the spring when the spring is in a charged, coiled state. Thereafter, when release is desired, the heating element can sever the fusible member to allow the spring to uncoil and drive operation of the insertion assembly. In other embodiments, compression and torsion springs can be utilized to puncture a gas cylinder to thereby drive pneumatic operation of various drug delivery device mechanisms/assemblies as described herein.

Figure 2:
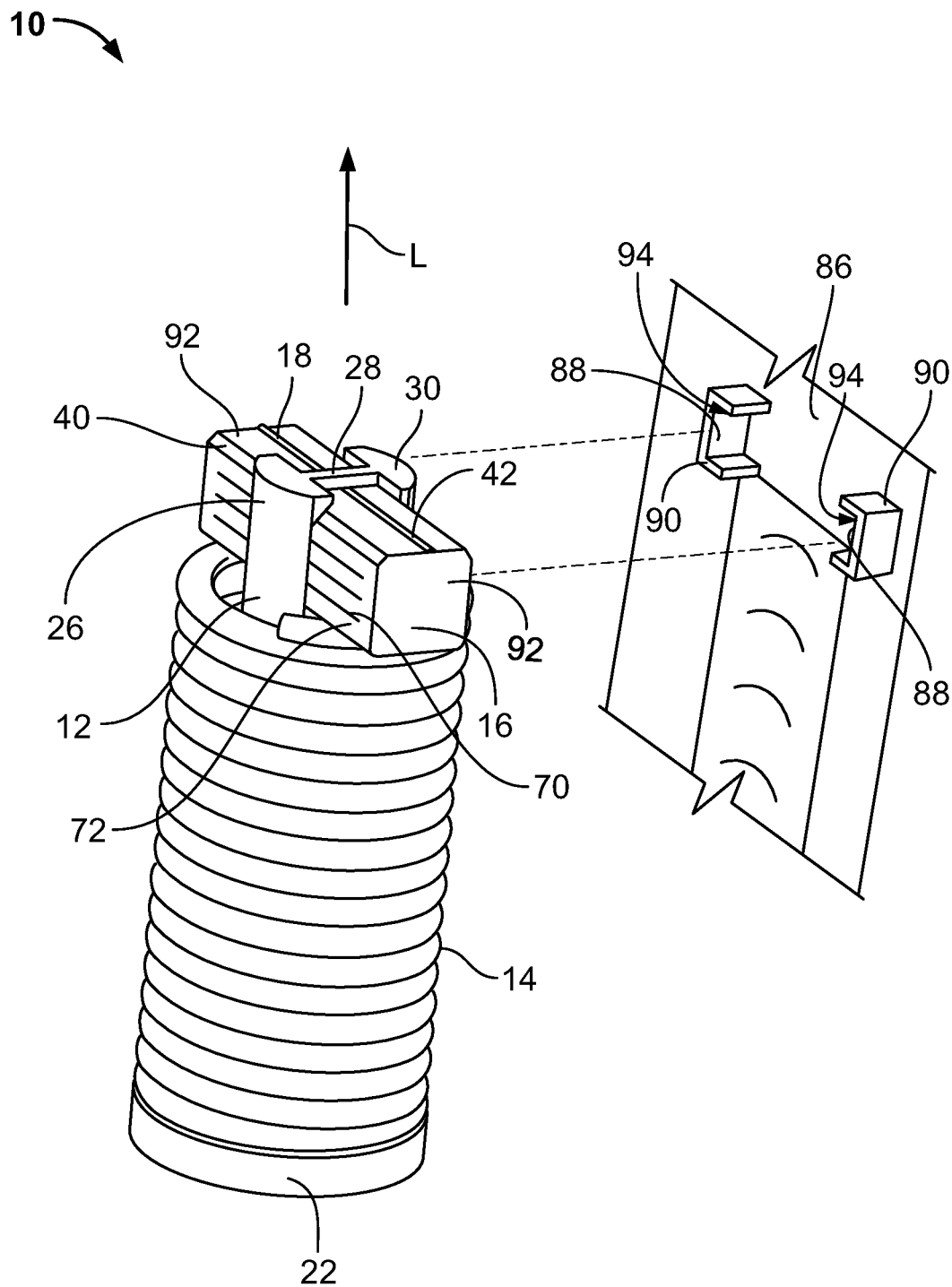
FIG. 2 is a perspective view of the compression spring drive assembly of FIG. 1 with a portion of a housing in accordance with various embodiments.

A first spring drive assembly 10 is shown in FIGS. 1 and 2 that includes a plunger rod 12, a compression spring 14, a retaining member 16, and a heating element 18. The plunger rod 12 has an elongate body 20 with an outwardly extending plunger face 22 at a distal end 24. The plunger rod 12 further has a forked configuration having a pair of opposing prongs 26 at a proximal end 32 of the body 20. The prongs 26 are joined by a fusible member 28 that extends along an end surface 30 of the plunger rod 12 to bridge the gap between the prongs 26. As shown, the fusible member 28 can be integrally formed with the plunger rod 12. In the illustrated form, each prong 26 includes an inwardly projecting foot 34 that connects to the fusible member 28 and has an angled bottom surface 36 so that the foot 34 has a triangular cross-sectional shape. The plunger rod 12 can have a cylindrical configuration as shown, with a cylindrical plunger face 22 extending radially outwardly from the cylindrical body 20, similar to a radial flange.

With this configuration, the proximal end 32 of the body 20 has a channel 38 (or hollow, or cavity) extending therethrough defined partially by inner surfaces of the prongs 26, feet 34, and fusible member 28. The channel 38 extends through the body 20 of the plunger rod 12 in a direction generally orthogonal to a longitudinal axis L of the plunger rod 12 and can have a longitudinal cross-sectional shape generally corresponding to the retaining member 16. As shown, the retaining member 16 has a box-shaped or bar-shaped configuration with chamfered edges 40 that are configured to engage the angled bottom surfaces 36 of the inwardly projecting feet 34 of the prongs 26 when the retaining member 16 is inserted into the channel 38.

To assemble the spring drive assembly 10, the compression spring 14 is axially aligned with the plunger rod body 20 and inserted thereon until a distal end 14a of the spring 14 abuts the plunger face 22. The spring 14 is then compressed until a proximal end 14b of the spring 14 clears the channel 38, at which point the retaining member 16 is inserted into the channel 38. As such, the spring 14 is held in a compressed configuration between the plunger face 22 and a lower surface of the retaining member 16 and the spring drive assembly 10 occupies a charged state. The fusible member 28 extends between the prongs 26 and prevents the spring 14 from forcing the retaining member 16 through the forked configuration of the rod proximal end 32.

In one form, the heating element 18 can be a wire 42 that extends along an upper surface 44 of the retaining member 16 and includes a portion that is disposed between the retaining member 16 and the fusible member 28. Further, the plunger rod 12, or at least the fusible member 28 thereof, may be constructed from a flame retardant plastic resin or a low melt temperature metal alloy, such that when the wire 42 is heated, as explained below, the wire 42 will cause the fusible member 28 to melt and sever and the spring 14 will force the retaining member 16 up between the decoupled prongs 26. If a low melt temperature metal alloy is used for the fusible member 28, the wire 42 can be insulated as commonly understood to maintain the electrical resistance and temperature of the wire 42 as the alloy melts.

Example materials for the components of the spring drive assembly 10 can include: polypropylene or 57% Bismuth/42% Tin/1% Silver alloy for the plunger rod 12 and the fusible member 28 thereof; and Nichrome (Nickel Chromium) for the wire 42; carbon steel wire or stainless steel wire for the spring 14; ceramic, glass, printed circuit board material, and/or high temperature (Thermoset) plastic resin for the retaining member 16. Further, if the retaining member 16 includes printed circuit board material, the wire 42 may be mounted to the printed circuit board material prior to assembly of the retaining member 16 into the spring drive assembly 10.

Figure 3:
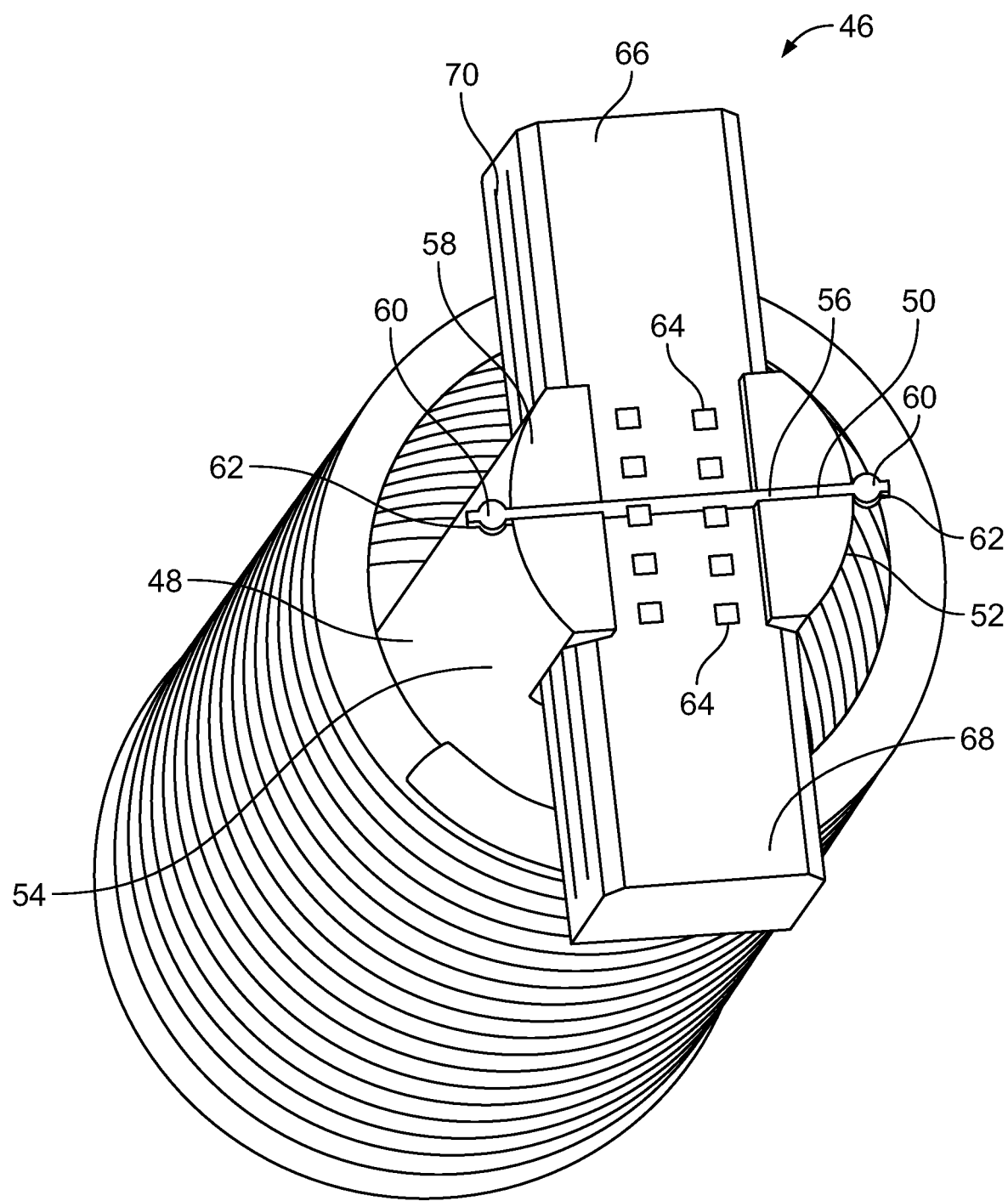
FIG. 3 is a perspective view of a second embodiment of a compression spring drive assembly in accordance with various embodiments.

An alternative configuration for a spring drive assembly 46 is shown in FIG. 3. A plunger rod 48 of this form is configured similarly to the plunger rod 12 discussed above and, as such, only the differences will be described herein. In this form, the fusible member is a fusible filament 50 of fusible metal that is coupled to a proximal end 52 of the plunger rod 48 so that the filament 50 holds prongs 54 of the proximal end 52 together. To achieve this, the filament 50 can extend within grooves 56 formed in end surfaces 58 of the prongs 54 and have retaining portions 60 on ends 62 thereof. As shown, the retaining portions 60 can be enlarged with regard to the size of the grooves 56, such as by being deformed by clamping or the like, can have bent portions, and so forth. The retaining portions 60 advantageously hold the prongs 54 at a fixed distance from one another to thereby restrict movement of a retaining member 68 inserted therebetween, as discussed in more detail below. In other versions, the filament 50 can be integral with the prongs 54 similar to FIGS. 1 and 2.

While the filament 50 of this form can be utilized with the wire 42 described above, in another approach, the heating element 18 can include a plurality of contact electrodes 64 exposed on or adjacent to an upper surface 66 of a retaining member 68. In the illustrated form, the contact electrodes 64 include opposing pairs of electrodes 64 aligned laterally with one another across the upper surface 66 of the retaining member 68 in a direction generally orthogonal to the longitudinal axis L of the plunger rod 48. The contact electrodes 64 can be selectively supplied with electricity via an electrical supply (not-shown), albeit with a broken circuit. With this configuration, the retaining member 68 can be inserted into the plunger rod 48 between the prongs 54 and positioned so that the filament 50 electrically contacts and engages two of the contact electrodes 64. As shown, a plurality of pairs of contact electrodes 64 can be provided so that the filament 50 can extend across the retaining member 68 in a range of widths while still contacting and engaging a pair of contact electrodes. With this configuration, the retaining member 68 need not be exactingly positioned with respect to the filament 50. When electricity is supplied to the contact electrodes 64, the filament 50 completes the circuit and, as such, is heated to melt and sever. Once the filament 50 is severed, the electrical circuit is broken, reducing or eliminating combustion risks associated with continued heating of the filament 50. Further, the heated zone is not in contact with plastic material. By one approach, the contact electrodes 64 can have closed, non-wetting surfaces to avoid adhesion of resolidifying metal of the filament 50, which may prevent or impair outward movement of the prongs 54. The contact electrodes 64 can be provided on a circuit board, such as a printed circuit board, which can form a portion or all of the retaining member 68 or can be mounted to the upper surface 66 thereof.

In this embodiment, the filament 50 may be constructed of a low temperature melting alloy such as 57% Bismuth/42% Tin/1% Silver alloy. Further, the diameter of the filament 50 may be as small as 0.05 mm so that the filament 50 can have a high electrical resistance and optimal current flow.

As discussed above, the retaining member 16, 68 in FIGS. 1-3 can have chamfered edges 40 that engage the angled bottom surfaces 36 of the inwardly projecting feet 34 of the prongs 26. The interaction of these surfaces transfer a significant amount of the load imparted on the retaining member 16, 68 by the spring 14 when the assembly 10, 46 is charged from the fusible member 28, 50 to the prongs 26, 54. This transfer of load, which can be optimized by suitable selection of angles, allows the fusible member 28, 50 size to be minimized, which in turn provides a fast, reliable, and low power consumption release of the assembly 10, 46.

The interaction between the feet 34 and the retaining member 16, 68 can further be utilized to moderate the speed at which the spring 14 drives the plunger rod 12, 48 to engage a stopper for a drug delivery operation, described in more detail below. Moderate or slow engagement of the stopper can in some versions advantageously avoid damage to the stopper and/or breakage of the syringe. After the stopper is engaged, the retaining member 16, 68 can be allowed to fully clear the prongs 26, 54 so that the spring 14 is freed of restraining forces and can drive the stopper with full force.

More specifically, as illustrated in FIGS. 1-3, some versions of the retaining member 16, 68 can include one or more engagement portions 70, which can be grooves and/or protrusions, that extend laterally along each side surface 72 thereof. The engagement portions 70 are spaced from one another on the side surfaces 72 along the longitudinal axis L of the plunger rod 12, 48 so that the feet 34 sequentially engage the engagement portions 70 as the retaining member 16, 68 is driven through the proximal end 32, 52 of the plunger rod 12, 48. The grooves or protrusions 70 preferably have a lateral width sized to fully receive or engage tips 74 of the feet 34 as the retaining member 16, 68. With a plurality of engagement portions 70 on either side of the retaining member 16, 68, engagement of the prongs 26, 54 moderates the speed that the retaining member 16, 68 is driven through the proximal end 32, 52 of the plunger rod 12, 48 and, therefore, the speed at which the plunger rod 12, 48 is driven to engage the stopper.

The depth or size of the engagement portions 70 determines the cantilever beam forces exerted by the feet 34 of the prongs 26, 54 as they slide down the retaining member 16, 68 during activation. The surface finish of the retaining member 16, 68, the size, material modulus, and angle of the feet 34/chamfered edges 40 can also be modified to optimize drag forces to achieve desired release times and speeds. Moreover, the number of engagement portions 70 and configuration of the various features can be optimized so that the plunger 12, 48 engages the stopper at a lower speed due to the friction between the feet 34 and the retaining member 16, 68 to impart less force on the stopper and container during initial impact. Further, the engagement portions 70 and configuration of the various features can be designed so that retaining member 16, 68 clears the feet 34 shortly after the plunger rod 12, 48 engages the stopper so that the spring is unrestrained to drive the stopper with full force during any extension remaining. Moreover, as the feet 34 sequentially engage the engagement portions 70, an audible signal can be generated. This audible signal can signal activation to a user. In other versions, the engagement portions 70 could be different textures, materials, and so forth.

Figure 4:
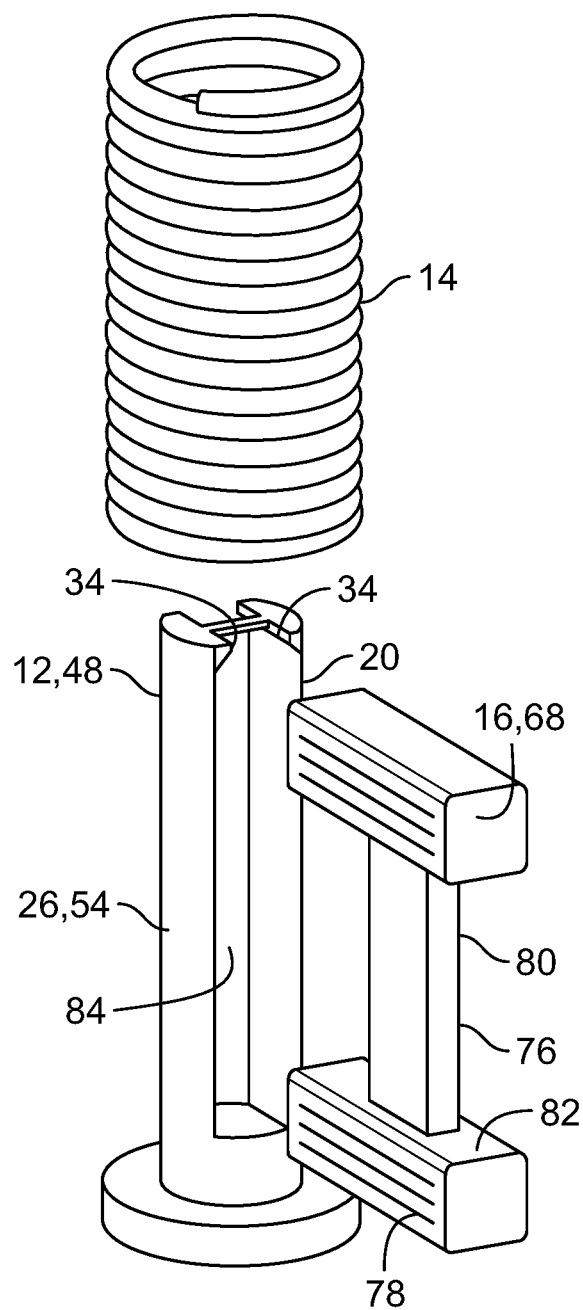
FIG. 4 is an exploded perspective view of an alternative embodiment of a compression spring drive assembly in accordance with various embodiments.

If desired, as shown in FIG. 4, the retaining member 16, 68 can include a trailing portion 76 with engagement portions 78, such as grooves or protrusions, configured to generate an audible signal upon interaction with the prongs 26, 54. The audible signal generated by the trailing portion 76 can in some versions correspond to an end of delivery signal to a user. The trailing portion 76 preferably has a neck 80 that does not engage the prongs 26, 54 so that the spring 14 can freely drive the plunger rod 12, 48 and a distal portion 82 with the engagement portions 78 sized and configured to engage the feet 34. With this configuration, the body 20 of the plunger rod 12, 48 can have a hollow configuration with a longitudinal cavity 84 sized to receive the trailing portion 76 therein when the assembly 10, 46 is in the charged configuration.

Turning back to FIG. 2, the assemblies 10, 46 can be received within a housing portion 86 of a drug delivery device. The housing portion 86 includes a recess or recesses 88 formed by upstanding walls 90 sized to receive lateral portions 92 of the retaining member 16, 68 therein to hold the retaining member 16, 68 in a fixed position within a suitable drug delivery device.

Adjacent to the recesses 88, the housing portion 86 has contacts 94, such as spring contacts or the like, that are mounted to electrically engage the heating element 18 when the retaining member 16, 68 is disposed within the recesses 88. The contacts 94 are coupled to a controller, discussed in more detail below, of the drug delivery device to receive signals so that the heating element 18 can be selectively energized when activation of the assembly 10, 46 is desired. The plunger body 20 extends away from the recesses 88 so that the plunger face 22 is disposed adjacent to a stopper within a reservoir, described in more detail below. In one approach, the housing portion 86 is configured so that the contacts 94 are disposed closely adjacent to the fusible member 28, 50 to reduce power consumption to heat and sever the fusible member 28, 50 by minimizing the length of the heating element 18.

Figure 5:
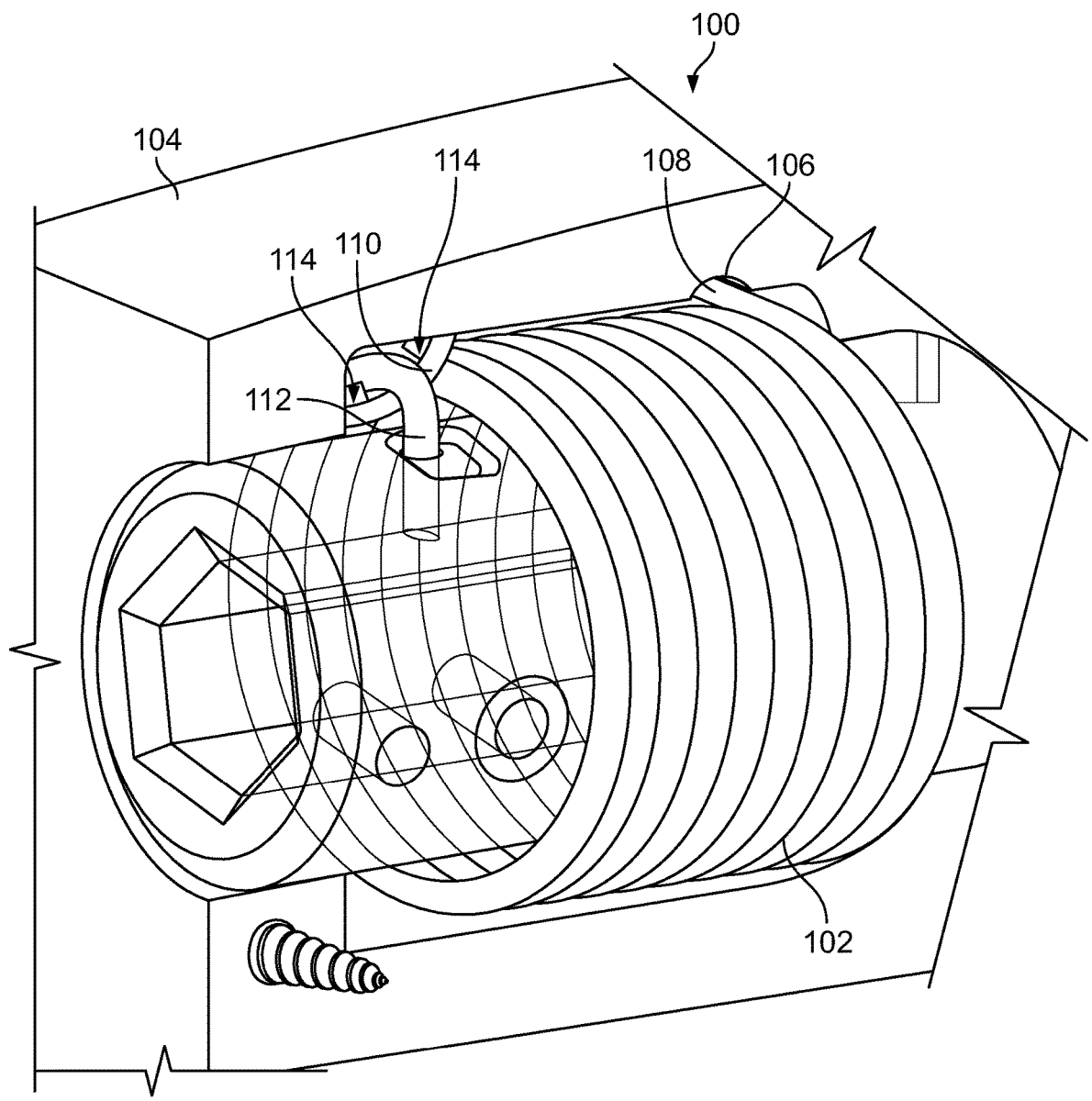
FIG. 5 is a sectional perspective view of one embodiment of a torsion spring drive assembly in accordance with various embodiments.

A torsion spring release mechanism 100 is shown in FIG. 5. In this embodiment, the mechanism 100 includes a torsion spring 102, a housing portion 104 having a catch 106 coupled to one end 108 of the spring 102, and a fusible member 110 coupled to the other end 112 of the spring 102. To charge the assembly 100, the coil of the spring 102 is tightened by winding with the first end 108 fixed in place by the catch 106. After the spring 102 is wound to a desired charge, the second end 112 of the spring 102 can be coupled to the fusible member 110 so that the spring 102 is held in the charged configuration. The second end 112 of the spring 102 can have a hooked configured to engage the fusible member 110. Other suitable configurations can alternatively be utilized.

Further, the mechanism 100 can include a heating element 112 that engages the fusible member 110 and contacts 114 that are coupled to the housing portion 104 and are configured to engage the heating element 112 for a selective supply of electrical energy. For example, the contacts 114 can be electrically coupled to a control circuit of a drug delivery device, as set forth in more detail below.

The spring release assemblies 10, 46, 100 described herein can be mounted within an on-body drug delivery device 200 to drive one or more components thereof as desired. For example, the torsion spring release mechanism 100 can be incorporated into a scotch yoke device to drive linear movement for needle/cannula insertion and/or drug delivery, can be coupled to a threaded drive rod assembly for driving linear movement for needle/cannula insertion or drug delivery, and so forth. Moreover, while FIG. 5 depicts a conventional torsion spring, the same concept can be implemented into a watch type tape spring, or any other suitable spring.

Figure 6:
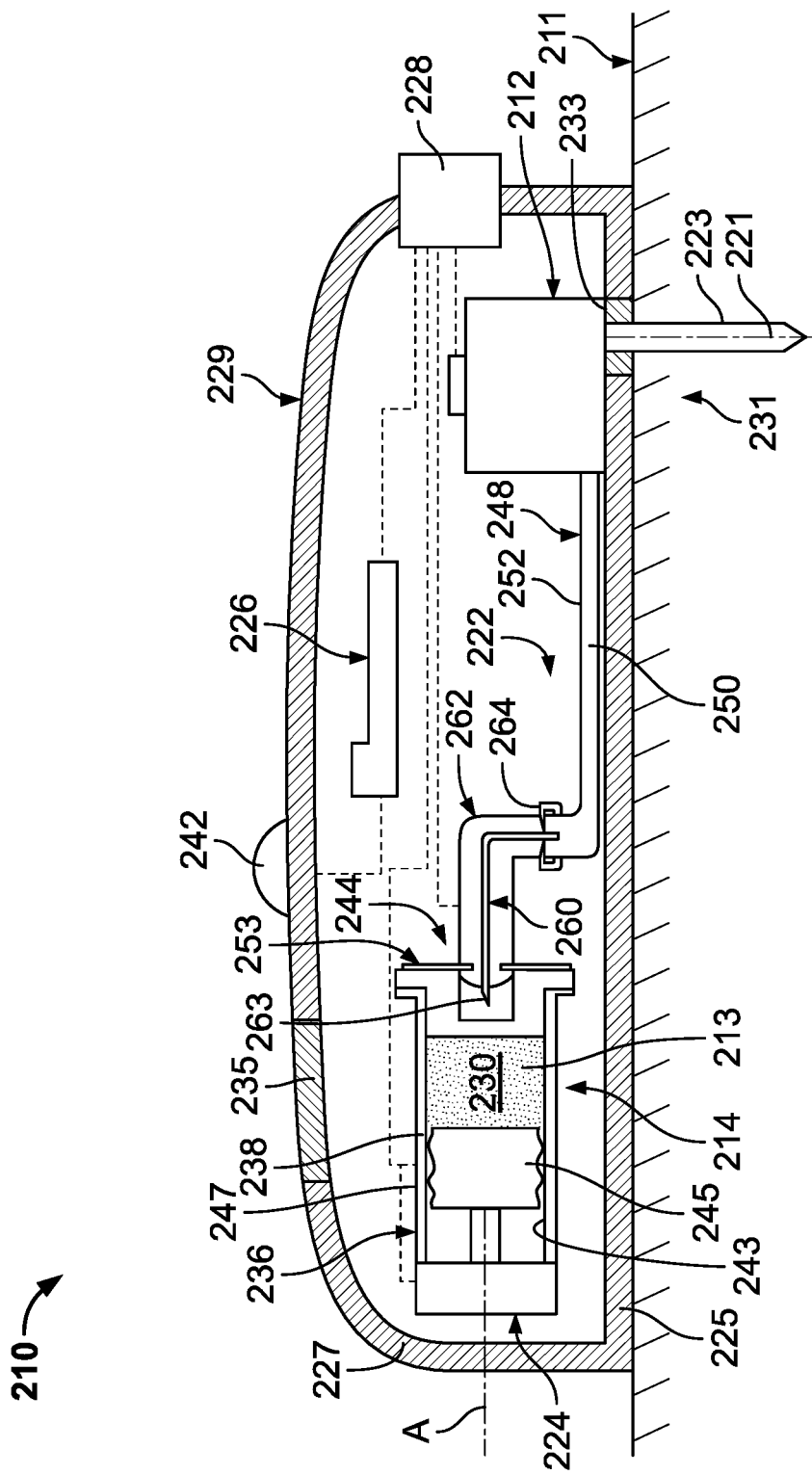
FIG. 6 is a side cross-sectional view of one embodiment of an on-body injector drug delivery device in accordance with various embodiments.

FIG. 6 is a schematic illustration of an on-body drug delivery device 210 that may be operated to subcutaneously or transdermally deliver a medicament to a patient. In the illustrated embodiment, the drug delivery device 210 is configured as a wearable drug delivery device, such as an on-body injector or an ambulatory infusion pump, and is releasably attachable to the patient's tissue 211 (e.g., the patient's skin). The drug delivery device 210 may be configured to automatically or after a predetermined delay deliver a fixed or a patient/operator-settable dose of a drug over a controlled or selected period of time. Furthermore, the drug delivery device 210 may be intended for self-administration by the patient, or may be operated by a formally trained healthcare professional or other caregiver to administer the injection.

Generally, the drug delivery device 210 may include an insertion mechanism 212, a container 214, a fluid pathway assembly 222, a drive mechanism 224, and a controller 226, each of which may be disposed within an interior space of a main housing 229. An actuator 228 (e.g., a user-depressible button, touchscreen, microphone, etc.) may protrude through or otherwise be disposed at an exterior surface of the housing 229 and may be configured to initiate operation of the drug delivery device 210 by activating, via mechanical, pneumatic, and/or electrical means (shown in dotted lines in FIG. 6), the insertion mechanism 212, the fluid pathway assembly 222, the drive mechanism 224, the controller 226, and/or other mechanisms and/or electronics. More specifically, the actuator 228 may operate as an input device that transmits an electrical and/or mechanical signal to the controller 226, which in turn may execute programmable instructions to control operation of the insertion mechanism 212, the drive mechanism 224, the fluid pathway assembly 222, and/or other mechanisms. In such embodiments, the controller 226 may include a processor (e.g., a microprocessor) and a non-transitory memory for storing the programmable instructions to be executed by the processor.

Still referring to FIG. 6, the housing 229 may include a bottom wall 225 configured to be releasably attached (e.g., adhered with an adhesive) to the patient's tissue 211, and a top wall 227 including one or more visual indicators 242 (e.g., lights, graphical displays, etc.) and/or a window 235 for viewing the container 214 and a medicament 213 contained therein. The one or more visual indicators 242 may be used to communicate information to the user about the operational state of the drug delivery device 210 and/or the condition of the medicament 213. An opening 231 may be formed in the bottom wall 225, and optionally a pierceable sterile barrier 233, such as a pierceable septum, may extend across the opening 231 to seal the interior of the housing 229 prior to use. In some embodiments, the pierceable sterile barrier 233 may be omitted, and instead a removable sealing member (not illustrated) may cover and seal close the opening 231 prior to use.

After the bottom wall 225 of the housing 229 is attached to the patient's tissue 211, the insertion mechanism 212 may be activated to move a delivery member from a retracted position within the housing 229 to a deployed position extending outside of the housing 229. In the present embodiment, this may include the insertion mechanism 212 inserting only a hard needle or a needle or trocar 221 and a hollow cannula 223 surrounding the trocar 221 through the pierceable sterile barrier 233 and into the patient's tissue 211, as illustrated in FIG. 6. Immediately or shortly thereafter, the insertion mechanism 212 may automatically retract the needle 221, leaving the distal open end of the cannula 223 inside the patient for subcutaneous delivery of the medicament 213. The needle 221 may be solid and have a sharpened end for piercing the patient's skin 211. Furthermore, the needle 221 may be made of a material that is more rigid than the cannula 223. In some embodiments, the needle 221 may be made of metal, whereas the cannula 223 may be made of plastic or another polymer. The relative flexibility of the cannula 223 may allow it to be disposed subcutaneously within the patient's tissue 211 for a period of a time without causing pain or significant discomfort to the patient.

The container 214, which in some contexts may be referred to as a primary container, may include a wall 238 with an interior surface 243 defining a reservoir 230 that is filled with the medicament 213 and an exterior surface 247. In some embodiments, the reservoir 230 may be pre-filled with the medicament 213 by a drug manufacturer prior to installation of the container 214 in the drug delivery device 210. In some embodiments, the container 214 may be rigidly connected to the housing 229 such that the container 214 cannot move relative to the housing; whereas, in other embodiments, the container 214 may be slidably connected to the housing 229 such that the container 214 can move relative to the housing 229 during operation of the drug delivery device 210. The container 214 may have an elongate, barrel-like or cylindrical shape extending along a longitudinal axis A. In embodiments where the drug delivery device 210 is configured as an on-body injector, the longitudinal axis A of the container 214 may be perpendicular or substantially perpendicular, or otherwise non-parallel, to a direction in which the insertion mechanism 212 inserts a delivery member such as the cannula 223 into the patient. This configuration may allow the on-body injector to have a generally planar, low-profile shape that can be worn by the patient without impeding the patient's movement. Initially, a stopper 245 may be positioned in the reservoir 230 at a proximal end 236 of the container 214. The stopper 245 may sealingly and slidably engage the interior surface 243 of the wall 238 of the container 214, and may be movable relative to the wall 238 of the container 214.

The volume of the medicament 213 contained in the reservoir 230 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL. The reservoir 230 may be completely or partially filled with the medicament 213. The medicament 213 may be one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

The assemblies 10, 46, 100 described above can be utilized to drive operation of one or more of the insertion mechanism 212, fluid pathway assembly 222, and/or drive mechanism 224 of the device 200 in response to an electrical control signal received from the controller 226.

More specifically, in some embodiments, the insertion mechanism 212 may include the torsion assembly 100 with the spring 102 initially retained in an energized state, and which is released upon depression of the actuator 228 in order to insert the needle 221 and cannula 223, or hollow needle, into the patient. This can be achieved, for example, by the controller 226 receiving the activation signal from the actuator 228 and causing the heating element 112 to heat and sever, releasing the spring 102. Furthermore, retraction of the needle 221 may be achieved by a return operation of the insertion mechanism 212. For example, the insertion mechanism 212 can be a scotch yoke mechanism. Alternatively, the assemblies 10, 46 can be modified to use the compression spring 14 to drive insertion along a linear path. In other embodiments, the assemblies 10, 46, 100 can be modified to use the springs 14, 102 to puncture a gas cylinder to thereby drive pneumatic operation of the insertion mechanism 212.

In further embodiments, the spring assemblies 10, 46 can provide the driving force for the drive mechanism 224. Specifically, the spring 14 may drive the plunger rod 12, 48 to push the stopper 245 along the longitudinal axis A from the proximal end 236 of the container 214 to a distal end 237 of the container 214 in order to expel the medicament 213 from the container 214. To activate the assembly 10, 46, a user can depress the actuator 228. The controller 226 receives the activation signal from the actuator 228 and causes the heating element 18 to heat and sever, releasing the spring 14. Following this release, the spring 14 may expand to move the stopper 245 through the reservoir 230 along the longitudinal axis A from the proximal end 236 of the container 214 to the distal end 237 of the container 214. Other configurations can utilize the rotary motion produced by the torsion spring assembly 100 to drive the drive mechanism 224. In other embodiments, the assemblies 10, 46, 100 can be modified to use the springs 14, 102 to puncture a gas cylinder to thereby drive pneumatic operation of the drive mechanism 224.

In yet further embodiments, one of the spring assemblies 10, 46, 100 can provide a drive mechanism for the fluid pathway assembly 222 to establish fluid communication between the container 214 and the insertion mechanism 212 via a sterile fluid flow path during operation of the drug delivery device 210. The fluid pathway assembly 222 may include a first end 244 connected to the container 214, a second end 248 connected to the insertion mechanism 212, and a fluid passage 250 extending between the first end 244 and the second end 248. In some embodiments the first end 244 of the fluid pathway assembly 222 may be connected to the container 214 via a clip member 253. The fluid passage 250 may be sterilized, and may be partially or entirely made of a flexible tubing 252. Initially, there may be slack in the flexible tubing 252 to allow the fluid pathway assembly 222 to move relative to the housing 229 and/or to allow components of the insertion mechanism 212 to which the fluid pathway assembly 222 is attached to move relative to the housing 229. In other embodiments, the assemblies 10, 46, 100 can be modified to use the springs 14, 102 to puncture a gas cylinder to thereby drive pneumatic operation of the fluid pathway assembly 222.

The first end 244 of the fluid pathway assembly 222 may include a container access needle 260 and an overmold member 262. In general, the overmold member 262 may serve as a mounting member or connection hub for the container access needle 260 and provide a portion of the container access needle 260 which does not access the reservoir 230 with an enlarged outer dimension, such as an enlarged outer diameter. The container access needle 260 may have a sharpened end or point 263, corresponding to a proximal end of the container access needle 260, and a distal end 264 in fluid communication with the fluid passage 250.

Figure 7:
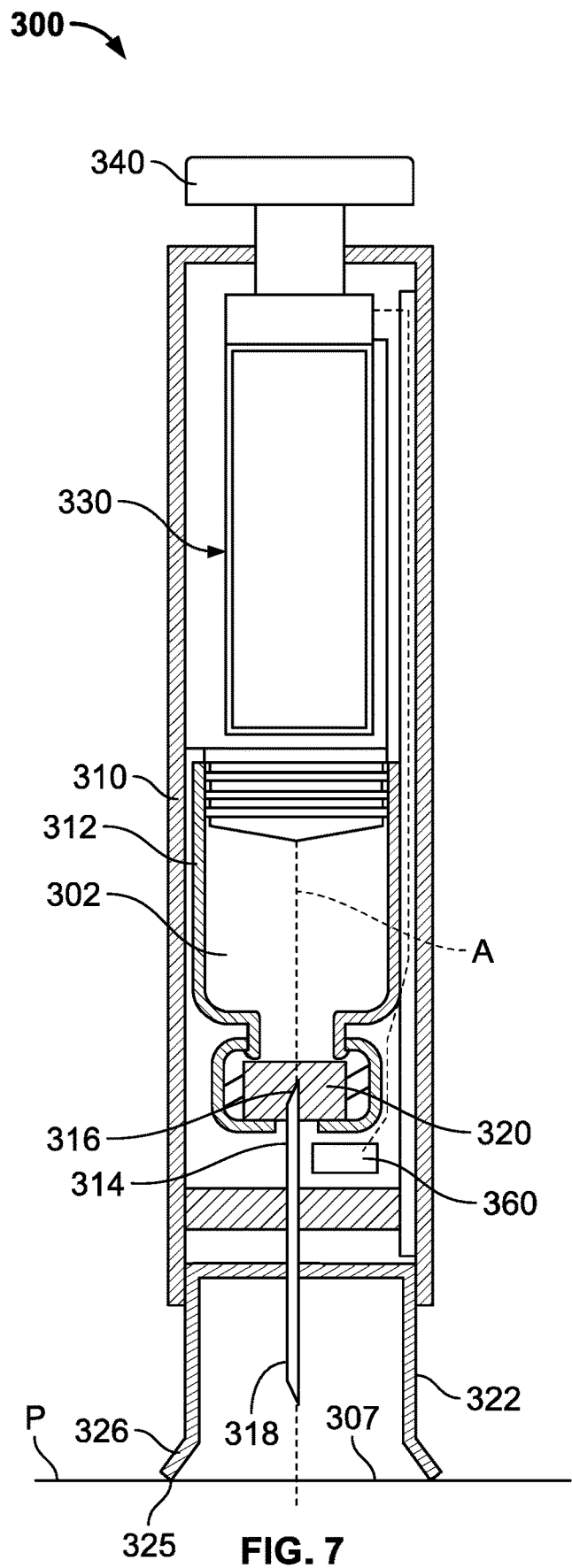
FIG. 7 is a side cross-sectional view of one embodiment of an autoinjector drug delivery device in accordance with various embodiments.

FIG. 7 depict an example autoinjector 300 incorporating the principles of the present disclosure and including a housing 310 in which may be disposed assemblies or structures that insert or enable insertion of a cannula 314 into the patient (not shown), and that inject a medicament 302 from a primary container 312 through the cannula 314 and into the patient.

In some embodiments, the cannula 314 has a first end 316 that may be connected or connectable in fluid communication to the primary container 312 and a second end 318 that may be inserted into the patient. The cannula 314 may be, for example, a metal needle sized such that the second end 318 is received under the skin so as to deliver a subcutaneous injection of the medicament within the primary container 312.

The first end 316 of the cannula 314 may be disposed through a wall 320 of the primary container 312, and thus be connected in fluid communication with the primary container 312. As illustrated, the first end 316 of the needle 314 may be disposed only partially through the wall 320 (which wall 320 may be a resealable septum or stopper, for example) such that the first end 316 of the cannula 314 may not be connected in fluid communication with the primary container 312 until the second end 318 is inserted into the patient. So configured, the wall 320 of this embodiment serves as a lock that maintains sterility of the primary container 312. Moreover, in some embodiments, once removed from the patient, the first end 316 may again become disconnected from fluid communication with the primary container 312. In such a circumstance, the first end 316 may be described as connectable in fluid communication with the primary container 312, although it will be recognized that there are other mechanisms by which the first end 316 of the cannula 314 may be connectable, but not connected, in fluid communication with the primary container 312.

In the disclosed embodiment, the drug delivery device 300 includes a needle guard 322 to limit access to the second end 318 of the cannula 314 when the drug delivery device 300 is not in use. According to certain embodiments, the needle guard 322 may have a biasing element (not shown) that urges the needle guard 322 away from the housing 310 and into a protracted position (not shown), such that a distal end 326 of the needle guard 322 extends beyond the second end 318 of the cannula 314 until if and when the cannula 314 is inserted into a patient. In fact, the injection of the cannula 314 may be actuated according to certain embodiments of the autoinjector 300 by disposing the distal end 326 of the needle guard 322 on or against the skin of the patient and applying a downward force.

According to certain embodiments, the distal end 326 of the needle guard 322 defines a distal surface 325 positioned in contact with the skin of the patient when the drug delivery device 300 is in use. As shown in FIG. 7, the distal surface 325 and an opening 307 of the needle guard 322 reside within a plane P that is substantially orthogonal to an axis A along which the cannula 314 extends when passing through the opening 307.

The autoinjector 300 may further include a controller 360. As shown in FIG. 6, the controller 360 can include a processor and a memory storing logic that is executable by the processor. More specifically, the memory may include one or more tangible non-transitory readable memories having logic (e.g., executable instructions) stored thereon, which instructions when executed by the processor may cause the at least one processor to carry out the actions that the controller is adapted to perform. Additionally, the controller 360 may include other circuitry for carrying out certain actions in accordance with the principles of the present disclosure.

Based on the foregoing, the drug delivery device 300 in FIG. 7 can be described as having a storage state as shown and a delivery state, which is not shown. In the storage state, the cannula 314 occupies a retracted position concealed within the protracted needle guard 322 of the housing 310. In the delivery state, as will be described, the cannula 314 occupies an extended position where its terminal end (i.e., the second end 318) extends out through the opening 307 of the needle guard 322 which occupies a retracted position. Accordingly, during use, and with the drug delivery device 300 occupying the storage state, the distal surface 325 of the needle guard 322 is placed against a patient's skin. A force is applied to the autoinjector 300 in a direction toward the patient to inject the cannula 314 into the patient. That is, as the force is applied, a counter force urges the needle guard 322 to retract into the housing 310 thereby allowing the second end 318 of the cannula 314 to extend out of the opening 307 and beyond the distal surface 325 of the needle guard 322 and into the patient. Simultaneously, the first end 316 of the cannula 314 fully penetrates the wall 320 to become in direct fluid communication with the reservoir 312.

In some embodiments, the drug delivery device 300 includes at least one delivery mechanism 330 that may be used to inject the medicament from the primary container 312 through the cannula 314 and into the patient. The actuator 340 may operate as an input device that transmits an electrical and/or mechanical signal to the controller 360, which in turn may execute programmable instructions to control operation of the spring release assemblies 10, 46, 100 to operate the delivery mechanism 330. Accordingly, upon user actuation of the actuator 340, the controller 360 may cause the heating element 18, 112 to heat and sever the fusible member 28, 50, 110, releasing the spring 14, 102 to drive movement of the delivery mechanism 330. In other embodiments, the assemblies 10, 46, 100 can be modified to use the springs 14, 102 to puncture a gas cylinder to thereby drive pneumatic operation of the delivery mechanism 330.

In some forms, the controller 226, 360 can be configured to delay operation of the assemblies 10, 46, 100 for a predetermined time. For example, upon receipt of an actuation signal from the actuator 228, 340, the controller 226, 360 can start a timer and cause the heating element 18 to heat after the timer ends to release the spring 14, 102. Additionally, the controller 226, 360 can be programmed to restrict operation in response to determining a fault or error in the device 210, 300. For example, the controller 226, 360 can determine that the medicament 213, 302 has expired, that the medicament 213, 302 has a temperature outside of a predetermined range, that a component of the device 210, 300 is faulty, and so forth. In some versions, the device 210, 300 can include skin contact mechanisms, including electrodes or mechanical latches, and the controller 226, 360 can restrict operation until the skin contact mechanisms indicate that the device 210, 300 is properly positioned on the patient.

The above description describes various assemblies and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 14667;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP 11b/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti- CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1 mAb (MDX-1106 (ONO-4538)); anti-PDGFRa antibody (IMC-3G3); anti-TGRβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV1023; NV1034 and NV1042 (Varghese et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the assemblies, drug delivery device, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, the spring release mechanisms described herein can be utilized in stent delivery systems, implant anchoring systems, biopsy harvesters, autolancets, bone injection guns, antenna, solar panel, and CubeSat deployment mechanisms, Radiosonde payload release, Linkwire NEA systems, and so forth.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the assemblies, drug delivery devices, systems, methods, and their elements.

What is claimed is:
1. A plunger rod drive mechanism for a drug delivery device, the plunger rod drive mechanism comprising:
 a plunger rod having an elongate body with an outwardly extending plunger face at a distal end and forked configuration at a proximal end;

a fusible member extending across the forked configuration at the proximal end of the plunger rod;

a spring mounted around the elongate body of the plunger rod abutting the plunger face;

a retaining member extending through the forked configuration of the plunger rod between the spring and the fusible member, the retaining member holding the spring in a compressed configuration; and a heating element configured to heat the fusible member and cause the fusible member to sever allowing the retaining member to pass through the proximal end of the plunger rod and releasing the spring to drive the plunger rod.

2. The plunger rod drive mechanism of claim 1, wherein the fusible member is (a) integral with the plunger rod or (b) mounted to the proximal end of the plunger rod.

3. The plunger rod drive mechanism of claim 1, wherein the forked configuration comprises opposing prongs having inwardly projecting feet configured to engage the retaining member, and the retaining member comprises a box-shaped member having chamfered edges configured to engage the inwardly projecting feet of the prongs.

4. The plunger rod drive mechanism of claim 3, wherein the retaining member includes engagement portions extending along exterior side surfaces thereof, where the inwardly projecting feet of the prongs are configured to sequentially engage the engagement portions to restrict movement of the retaining member through the proximal end of the plunger rod.

5. The plunger rod drive mechanism of claim 1, wherein the heating element comprises a heating wire extending along a top surface of the retaining member and between the retaining member and the fusible member or contact electrodes exposed on an upper surface of the retaining member.

6. The plunger rod drive mechanism of claim 1 in combination with a plunger assembly, the plunger assembly further comprising:

a reservoir; and a stopper received within the reservoir, the plunger face of the plunger rod configured to engage the stopper.

7. A method of assembling a plunger rod drive mechanism for a drug delivery device, the method comprising:

providing a plunger rod having an elongate body with an outwardly extending plunger face at a distal end and forked configuration at a proximal end, and a fusible member extending across the forked configuration at the proximal end of the plunger rod;

mounting a spring coaxially around the elongate body of the plunger rod abutting the plunger face;

compressing the spring to a compressed configuration;

inserting a retaining member through the forked configuration of the plunger rod between the spring and the fusible member, the retaining member holding the spring in a compressed configuration; and disposing a heating element adjacent to the fusible member, the heating element being selectively operable to cause the fusible member to sever to thereby allow the retaining member to pass through the proximal end of the plunger rod and releasing the spring to drive the plunger rod.

8. The method of claim 7, wherein providing the plunger rod comprises (a) providing a plunger rod with the fusible member being integral with the proximal end or (b) providing a plunger rod and mounting the fusible member to the proximal end.

9. The method of claim 7, further comprising engaging the retaining member with inwardly projecting feet of opposing prongs of the forked configuration.

10. The method of claim 7, wherein disposing the heating element adjacent to the fusible member comprises (a) disposing a wire along a top surface of the retaining member and between the retaining member and the fusible member or (b) disposing a plurality of contact electrodes on an upper surface of the retaining member to electrically engage the fusible member.

* * * * *